United States Patent
Brune et al.

(10) Patent No.: US 10,859,479 B2
(45) Date of Patent: Dec. 8, 2020

(54) NON-DESTRUCTIVE STALK AND ROOT CONTACT SENSOR WITH VARIABLE RATE TENSIONER

(71) Applicant: PIONEER HI-BRED INTERNATIONAL, INC., Johnston, IA (US)

(72) Inventors: Philip F. Brune, Parkland, FL (US); Jeffrey Dale Wille, Ankeny, IA (US)

(73) Assignee: PIONEER HI-BRED INTERNATIONAL, INC.

( * ) Notice: Subject to any disclaimer, the term of this patent is extended or adjusted under 35 U.S.C. 154(b) by 218 days.

(21) Appl. No.: 16/193,102

(22) Filed: Nov. 16, 2018

(65) Prior Publication Data

US 2019/0195762 A1 Jun. 27, 2019

Related U.S. Application Data

(60) Provisional application No. 62/608,964, filed on Dec. 21, 2017.

(51) Int. Cl.
| | |
|---|---|
| *G01N 3/20* | (2006.01) |
| *A01B 79/00* | (2006.01) |
| *A01H 1/04* | (2006.01) |
| *G01N 33/483* | (2006.01) |
| *G01B 7/16* | (2006.01) |
| *G01N 3/06* | (2006.01) |
| *G01B 5/30* | (2006.01) |

(52) U.S. Cl.
CPC .............. *G01N 3/20* (2013.01); *A01B 79/005* (2013.01); *A01H 1/04* (2013.01); *G01B 5/30* (2013.01); *G01B 7/16* (2013.01); *G01N 3/06* (2013.01); *G01N 33/4833* (2013.01)

(58) Field of Classification Search
CPC ........ G01N 3/06; G01N 3/20; G01N 33/4833; A01D 45/16; G01L 1/10; A01H 1/04; G01B 5/30; G01B 7/16
See application file for complete search history.

(56) References Cited

U.S. PATENT DOCUMENTS

| | | | |
|---|---|---|---|
| 5,044,210 A | * | 9/1991 | Kuhn ..................... A01D 75/00 73/865.3 |
| 7,401,528 B2 | | 7/2008 | Deppermann et al. |
| 7,987,735 B2 | | 8/2011 | Mann, III et al. |

(Continued)

FOREIGN PATENT DOCUMENTS

| | | |
|---|---|---|
| EP | 2 035 805 B1 | 12/2007 |
| WO | 2016/205244 A1 | 12/2016 |
| WO | 2017/172889 A1 | 10/2017 |

OTHER PUBLICATIONS

Guo, Qingqian, et al.: "A Non-Destructive and Direction-Insensitive Method Using a Strain Sensor and Two Single Axis Angle Sensors for Evaluating Corn Stalk Lodging Resistance", Sensors, Jun. 6, 2018 (Jun. 6, 2018), vol. 18, No. 1852, pp. 1-11. (http://dx.doi.org/10.3390/s18061852).

*Primary Examiner* — Francis C Gray

(57) ABSTRACT

An apparatus and methods for non-destructively analyzing the strength of plant roots and stalks, and uses of this information in plant breeding, crop production, and detection of plant pathology. The apparatus and methods involve the use of a variable rate tensioner that may be automatically or remotely adjusted based on crop conditions.

27 Claims, 15 Drawing Sheets

(56) References Cited

U.S. PATENT DOCUMENTS

| | | | | |
|---|---|---|---|---|
| 8,215,191 | B2* | 7/2012 | Tragesser | A01D 43/085 |
| | | | | 73/862.627 |
| 8,900,808 | B2* | 12/2014 | Ching | C12Q 1/6895 |
| | | | | 435/6.1 |
| 9,322,629 | B2 | 4/2016 | Sauder et al. | |
| 10,337,951 | B2* | 7/2019 | Cook | G01M 5/0075 |
| 2007/0294994 | A1* | 12/2007 | Deppermann | A01G 7/00 |
| | | | | 56/27.5 |
| 2014/0331631 | A1* | 11/2014 | Sauder | G01B 21/10 |
| | | | | 56/10.2 R |
| 2015/0319929 | A1* | 11/2015 | Hendrickson | A01D 45/023 |
| | | | | 33/504 |

* cited by examiner

NON-DESTRUCTIVE STALK AND ROOT CONTACT SENSOR WITH VARIABLE RATE TENSIONER

TECHNICAL FIELD

Embodiments of the present disclosure relate to an apparatus and methods for non-destructively analyzing the strength of plant roots and stalks, and uses of this information in plant breeding, crop production, and detection of plant pathology.

BACKGROUND

There is a need to non-destructively assess the strength of plant roots and stalks in order to use this information for plant breeding, crop production, and detection of plant pathology.

SUMMARY

An apparatus and methods for non-destructively analyzing the strength of plant roots and stalks is described herein, together with uses of information obtained from the apparatus and methods in plant breeding, crop production and plant pathology. Uses include crop selection, assessment of stalk and root lodging risk, and detection of pathological conditions that afflict the stalk or root systems. The apparatus and methods involve use of an adaptive tensioner to adjust sensor functionality in real time based on changing field and crop conditions.

BRIEF DESCRIPTION OF THE DRAWINGS

The present disclosure is illustrated by way of example, and not by way of limitation, in the figures of the accompanying drawings and in which.

DEFINITIONS

Figure 1:
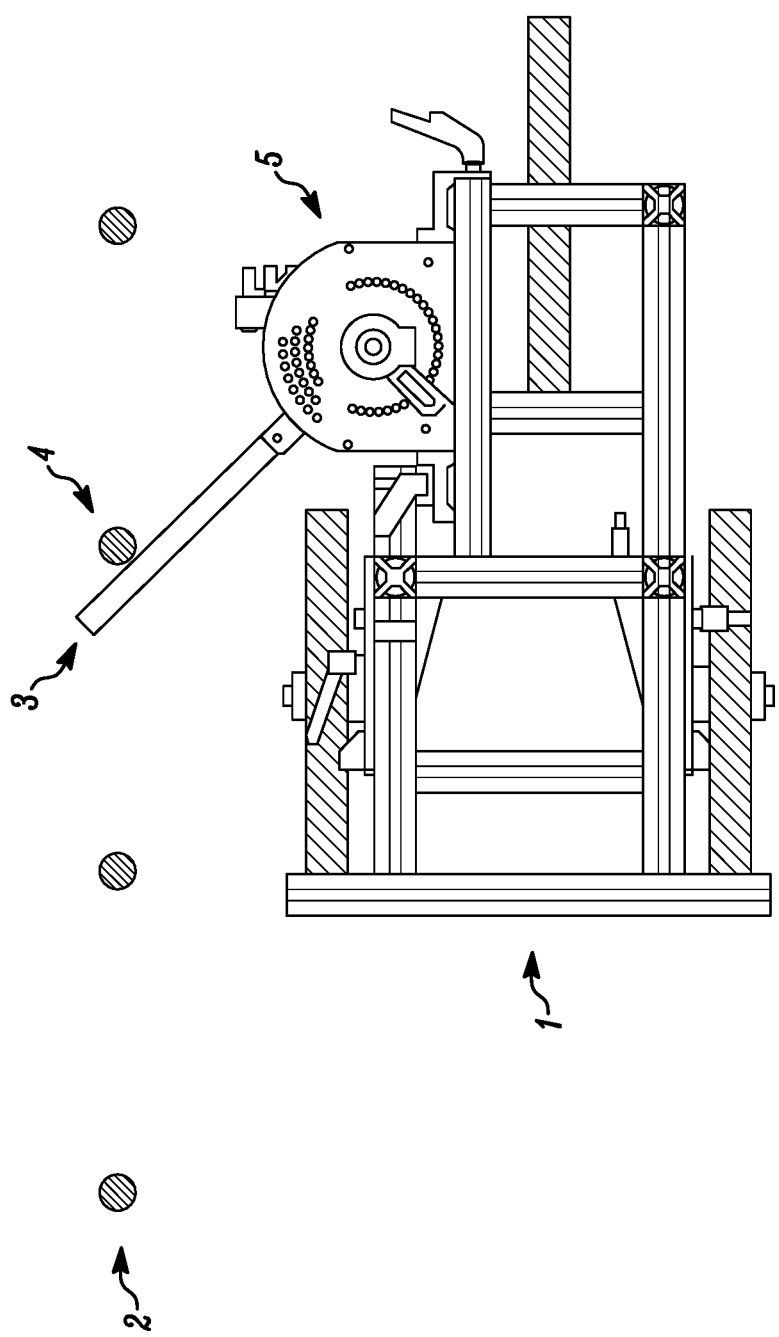
FIG. 1 shows, in one embodiment of the sensor system, the system positioned on a farm vehicle and moving through rows of plants.

"Anchorage strength", or "root strength", means the mechanical resistance to failure of the root-soil volume.

"Anchorage stiffness" means the mechanical resistance of the root-soil volume to rotation.

"Automatically" refers to an action being taken by a computer or system without human intervention. For example, adjustment of the embodiments of the assay devices described herein would occur during operation without operator intervention.

"Contact element" means a component of the sensor system that physically interacts with a plant stalk.

"Data file" means an electronic file that contains numerical data.

"Deformable" means that the mechanical force resulting from the mechanical interaction between the contact element and the plant is sufficient to cause motion of the contact element, resulting in flexure of the contact element or rotation of the adjustable tensioner from its initial resting state. Non-deformable means that the rigidity of the contact element is sufficient to prevent a significant degree of flexure.

"Farm vehicle" means any machinery capable of traversing a field, including but not limited to a planter, tractor, rover, harvester, all-terrain vehicle, sprayer, or fertilizer.

"Grain" means the harvested seeds of a row crop used for food.

"Load Cell" means a transducer that is used to create an electrical signal whose magnitude is directly proportional to the mechanical force being measured. Load cells include, but are not limited to, hydraulic load cells, pneumatic load cells, piezoelectric load cells, vibrating wire load cells, capacitive load cells and strain gauge load cells.

"Mechanical Resistance" means a measure of how much a structure resists motion when subjected to mechanical force.

"Mechanical stiffness" means the resistance of an object to an applied mechanical deformation.

"Mechanical strength" means the ultimate applied load capacity of an object, structure, or material.

"Planting density" means the as-planted plant population rate of a crop, typically measured in plants/acre.

"Proximal to" means nearby spatially within a relevant length scale.

"Remotely" means, with respect to the adjustment of the flex of a contact element, that the flex of the contact element may be changed automatically without operator involvement, or by the operator while the operator remains in the agricultural vehicle. If the agricultural vehicle is robotic, then it means that the flex of a contact element may be automatically changed without physical contact by a human.

"Root Lodging" means the irreversible mechanical deformation of a plant's subterranean support structure. It is a physical process by which wind action on a plant's above-ground structure generates an aerodynamic load, whose resultant bending moment surpasses the root-soil anchorage capacity, causing a rotation of the below-ground support base and angling the plant stalk from a vertical position.

"Rotational Encoder" means an electro-mechanical device that converts the angular position or motion of a shaft to an analog or digital signal. The rotational encoder may be absolute or incremental (relative). A rotational encoder may also be referred to as a shaft encoder.

"Rotational Sensor" means a sensor operably connected to the contact elements of the sensor system. The rotational sensor may comprise one or more of a rotational encoder, load cell, spring or gyroscopic sensor. In addition, the rotational sensor may be part of a system for an adaptive contact element, wherein the sensor can detect information that is used to control flex in one or more of the contact element and its mounting fixture on the attachment bar.

"Soil bulk density" means the mass per unit volume of dry soil.

"Soil cohesion" means the component of soil shear strength that arises from electrostatic bonds between smaller particles (e.g. silt and clay) and/or capillary forces in water menisci that bridge particles.

"Soil compaction" means the densification of soil due to displacement of air from pores between soil grains.

"Soil consolidation" means the densification of soil due to displacement of water from pores between soil grains.

"Soil hydrological properties" mean the saturated hydraulic conductivity and surface-level water holding capacity of soil.

"Soil mechanical resistance" means the ability of soil to retain its structure when subjected to mechanical forces arising from interaction with external bodies. The mechanical resistance is a composite measure that implicates several other soil properties, including soil bulk density, soil (volumetric) moisture, soil shear strength, soil cohesion, and susceptibility to soil compaction and soil consolidation.

"Soil moisture content" means the extent to which pores between soil particles are filled with water, and can be defined volumetrically or gravimetrically.

"Soil properties" means soil properties such as soil mechanical resistance, soil hydrological properties, soil moisture content and the like.

"Soil shear strength" means the magnitude of shear stress that a soil can sustain, arising from interparticle friction, interlocking, and soil cohesion.

"Stalk failure moment" means the applied bending moment at which a single plant undergoes stalk lodging.

"Stalk failure work" means the applied mechanical work necessary to cause stalk lodging in a single plant. It is calculated by integrating the applied bending moment versus stalk rotation curve.

"Stalk lodging" means the breakage of a stalk below the grain. In corn, this would be defined as breakage of the stalk below the ear, but above the roots.

"Stalk stiffness" means the mechanical resistance of a plant stalk to bending deformation.

"Spring constant", or "Spring Tension", or "Spring rate" means the stiffness of a mechanical spring, typically expressed as a proportionality constant to relate its extension or deformation to the applied force.

"Tensioner" means a device capable of providing resistance to rotational or linear motion.

DETAILED DESCRIPTION

Stalk lodging is a significant concern of corn growers, and annual corn yield losses due to stalk lodging in the U.S. range between 5 and 25%. Severe weather is a major cause of stalk lodging. Hard driving rains in conjunction with strong winds can create strong directional forces that can cause stalk breakage. Insect stalk damage that weakens stalks, such as corn borer infection that tunnels into the stalk or ear shank, can be a sole or contributing factor to stalk lodging. Likewise, fungal diseases such as stalk rot can weaken the stalk tissue and can also be a sole or contributing factor to stalk lodging.

Hybrids vary in genetic resistance against insect damage and stalk rot organisms, and so hybrid selection can be a useful deterrent against lodging risk. Plant population levels can also influence the ability of a crop to withstand stalk lodging. Plant-to-plant competition for light, nutrients, and water enhances the competition for carbohydrates between the stalk and ear within the plant, thus reducing the vigor of the cells in the stalk and predisposing them to invasion by stalk rot. High density plant populations can also limit the resources available for development of structural tissue, which weakens the stalks mechanically and predisposes plants to stalk lodging.

Soil moisture is also a factor in stalk lodging. Excessive soil moisture retards root growth and development, leading to a less than optimum root system which cannot adequately support plant growth. On the other hand, drought conditions stress the crop and enhance the development of stalk rot by reducing movement of sugars to the root system. Therefore, accurate estimation of stalk lodging risk on a plant to plant basis can help growers make better drainage and/or irrigation decision. Planting date decisions can also be utilized to reduce stalk lodging risk, because early planted corn is typically less susceptible to stalk lodging for a variety of reasons.

Root lodging is also a concern of corn growers, with annual yield losses comparable to those caused by stalk lodging. Root lodging can be viewed as a plant's resistance to lodging as a structural failure of the root-soil anchorage system, causing the plant to deviate from a vertical plane of growth. Like stalk lodging, root lodging is a complex phenomenon that depends strongly on both crop genetics and environmental factors. Significant rain increases soil moisture and reduces soil shear strength, a key component of anchorage, making plants susceptible to strong winds that can induce root lodging via anchorage failure. The root architecture is also a key factor in root lodging, with the size of the structural root zone (i.e. the volume enclosed by the thicker nodal roots in the upper 6 inches of the soil for maize) significantly influencing anchorage strength. Corn root worm feeding, which compromises these thicker structural roots, can significantly increase susceptibility to root lodging. Finally, higher density plant populations and excessive soil moisture during development can also result in plants with diminished root architectures and increased susceptibility to root lodging.

For plant breeders selecting crops for stalk and root lodging resistance, direct measurement of plant lodging resistance at high throughput can make it easier to separate genetic, environmental, and pathological factors. Additionally, such a measurement system that functions in a non-destructive manner can be a valuable management tool for grain and seed growers to determine which management practices would be most likely to reduce their root and stalk lodging risk. The identification of weakening stalks and/or weakening roots at different times during the growing season can help a grower identify which agronomic practices to utilize to reduce lodging risk in both that season and in future growing seasons.

The apparatus and methods described herein include a device that can be mounted on a farm vehicle and, depending on its configuration and the field conditions, be utilized to non-destructively measure a plant's stalk or root strength. These measures can then be combined with a model that incorporates location-specific data such as weather patterns and soil properties to calculate a broader assessment of stalk and root lodging resistance or susceptibility. This assessment can be utilized to improve variety selection, planting density selection, planting depth selection, and even crop type to be planted in the field.

Furthermore, the apparatus and methods described herein can be used in conjunction with other apparatus and methods that assess soil mechanical resistance to provide a more complete measurement of anchorage strength and root lodging resistance that incorporates high resolution characterization of the local soil conditions.

The apparatus and methods described herein can be used to quantify a plant's stalk and root lodging resistances, which together determine a plant's overall lodging resistance. It can also determine an 'average' bio-mechanical health level of plants in a field that can be used as a baseline to identify plants that deviate significantly and are perhaps either afflicted with disease or insect feeding, thereby giving a more accurate assessment of plant health and environmental conditions for both above-ground and below-ground portions of the plant.

Stalk and root lodging afflict a variety of cereal crops, including maize (*Zea mays* L.), soybeans (*glycine max*), sunflower (*Helianthus annus*), sorghum (*Sorghum bicolor*), canola (*Brassica napus*), wheat (*Triticum aestivum* L.), barley (*Hordeum vulgare* L.), rice (*Oryiza sativa*) and oats (*Avena sativa* L.).

DESCRIPTION OF VARIOUS EMBODIMENTS OF THE STALK AND ROOT LODGING ASSAY DEVICE

Stalk and Root Contact Sensor with Adaptive Tensioner

In one embodiment, as shown in FIG. 1, the sensor system is positioned on a farm vehicle (1) so that the sensor contact element (3) travels in between or beside the row or rows of plants (2). A plurality of variably spaced contact elements (3) are positioned so that one or more of the contact elements (3) may contact the stalk (4) of the plant as the farm vehicle (1) travels in a forward direction down the row. In this embodiment, the contact element (3) may be operably connected to a variable rate spring (5) that can be adjusted as the vehicle or farm equipment is in motion. In general terms, the system consists of a mechanical contact element that is connected to one subsystem that transduces the mechanical force applied to it and to another sub-system that dynamically and automatically varies the mechanical stiffness of the contact element. Typically, this occurs at the point of rotation of the contact element, such as through alteration of a spring loaded rotational shaft or a pneumatic, magnetic or electrical element. In most cases the contact element will be effectively rigid with the deformable base with variable stiffness providing the degrees of tension adjustment. However, in some embodiments, the dynamic and automatic variation of the mechanical stiffness may be effected through a change in the flexure of the contact element. For example, the contact element may be deformable and a piezoelectric sensor or strain gauge may be used with the contact element to measure the angular rotation and/or flexure resulting from the motion of the contact element as it engages the plant. In this type of embodiment, a more flexible material for the contact element will be more suitable, and it may also be desirable to dynamically adjust the stiffness on-the-go to increase or reduce the flexural stiffness of the contact element as needed. The contact element may be made of any suitable material, such as metal, plastic, polymer, ceramic, graphite or carbon fiber, provided the selected material meets the rigidity or deformability requirement stated above.

Figure 2:
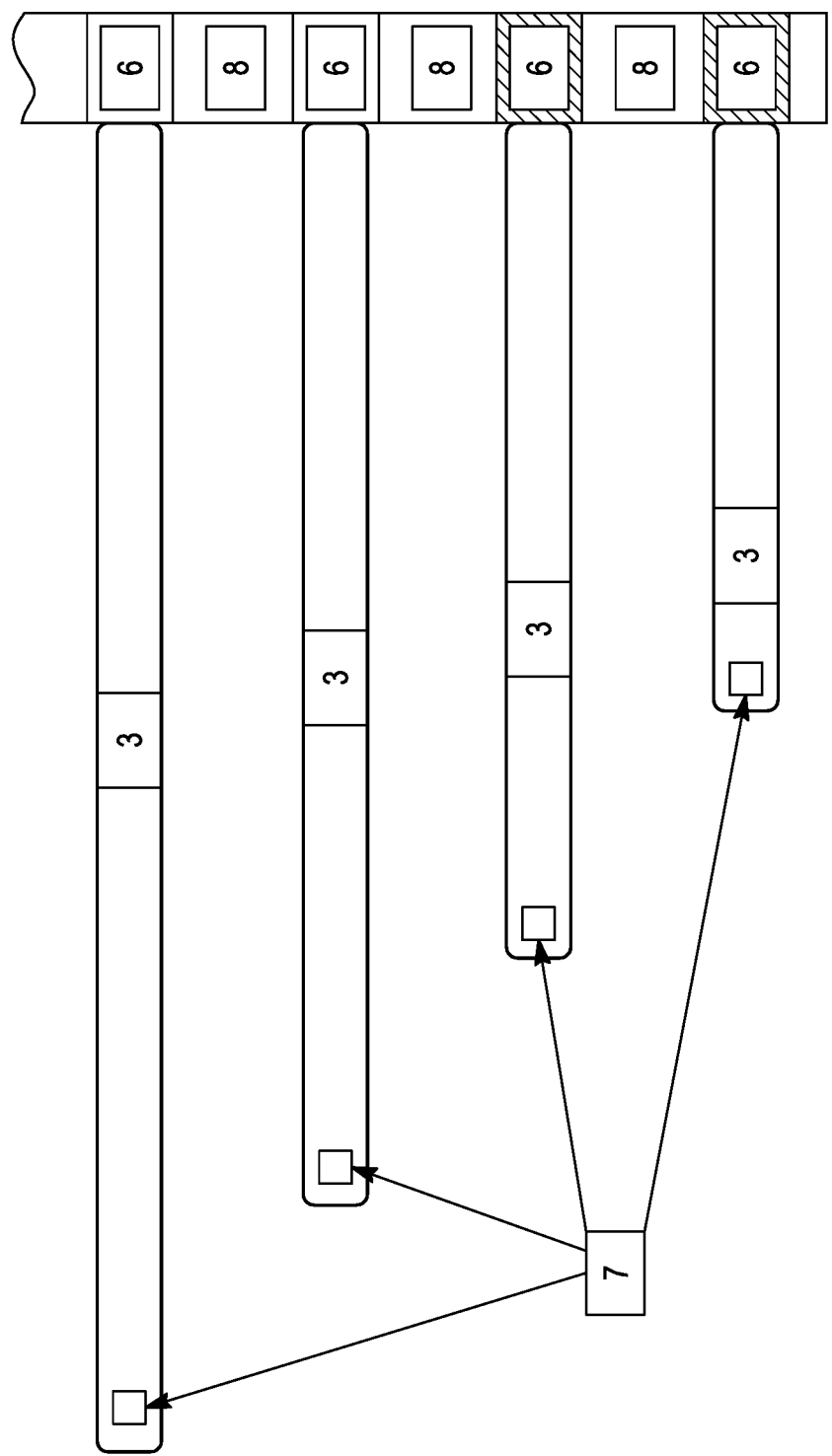
FIG. 2 shows, in one embodiment of the sensor system, a detailed view of sensor contact elements and sensor components.

FIG. 2 shows a detailed view of a sensor contact elements (3) showing sensor components. In this embodiment, there is an array of four contact elements (3), which are each connected to a spring loaded rotational encoder (6). In between each rotational encoder (6) is a rotational damper (8). In some embodiments, the rotational dampers are one-way rotational dampers oriented to absorb impact on the return, while not absorbing force when the contact element (3) engages the plant stalk. At the end of each contact element (3) is an accelerometer that measures the dynamic movement and/or vibrations, and can be used to quantify in approximate terms the severity of the initial impact between the contact element and the plant stalk.

The variable rate tensioner, whether operated as a result of a variable rate spring (5) as in FIG. 1, or in other embodiments, by utilization of a pneumatic, hydraulic, magnetic or electronic system to enable more rapid and finely resolved remote adjustment of tension on the contact element (3), may be adjusted so that an appropriate amount of mechanical stiffness is present in the sensor element to obtain a useful reading of the root or stalk stiffness and enables precise adjustment of the stiffness of the contact elements (3) to avoid excessive applied forces that could result in breakage of the stalks or permanent deformation of the root-soil anchorage zone.

Figure 3:
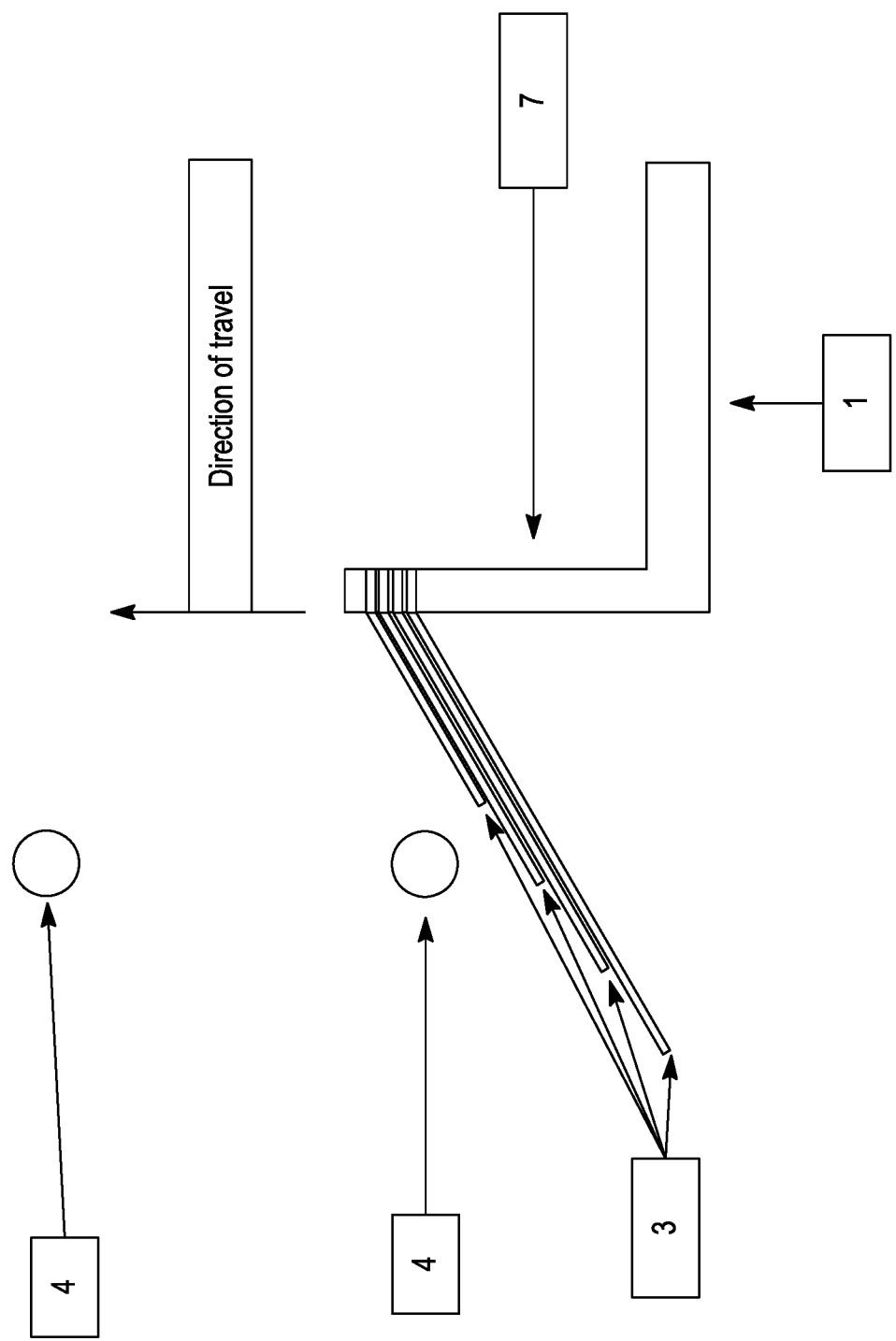
FIG. 3 shows, in one embodiment of the sensor system, the orientation of the contact elements relative to the direction of travel past the plant stalks, as well as the attachment bar that connects the sensor system to an agricultural vehicle. The contact elements are positioned in a vertically stacked orientation as shown in FIG. 2, in order to avoid interference between contact elements.

FIG. 3 shows, in one embodiment, the orientation of the contact elements (3) relative to the direction of travel past the plant stalks (4), as well as the attachment bar (7) that connects the sensor system (3) to an agricultural vehicle.

Any number of contact elements (3) may be used, such as from 2 to 20 contact elements. For example, the use of an array of four contact elements (3), such as in the embodiment shown in FIGS. 2 and 3, provides enough contact elements to ensure that some of the contact elements will contact the crop stalk (4). The use of a plurality of variable length contact elements (3) enables the gathering of information on the location of the crop stalk relative to the attachment bar (7). An array of contact elements (3) that spans different segments of the plant, up to an including the full plant height, can be used to determine plant height and/or the location of the ear on a mature plant.

The contact elements (3) may be positioned at a substantially horizontal position relative to the ground, and therefore engage the plant stalk (4) at a substantially perpendicular angle. In other embodiments, the contact elements (3) may be positioned at a downwardly sloped angle to engage the plant at approximately 30 degrees below the perpendicular plane. In alternative embodiments, the contact elements (3) may be positioned to engage the plant anywhere between 1 and 75 degrees below the perpendicular plane. In other embodiments, the contact elements (3) may be upwardly sloped at an angle to engage the plant anywhere between 1 and 75 degrees above the perpendicular plane. In some cases, it may be desirable to use an array of contact elements (3) to sense the location of ears of corn, and so a perpendicular to upwardly sloping array of contact elements (3) would be beneficial. In other cases, it may be preferable to contact only the stalk (4), and so a downwardly sloping array of contact elements (3) would be beneficial. If desired, a large full 'whisker' array comprising a combination of upwardly sloping, perpendicular and downwardly sloping contact elements (3) may be utilized. Each contact element is positioned in a manner that avoids interference with adjacent contact elements.

Figure 4:
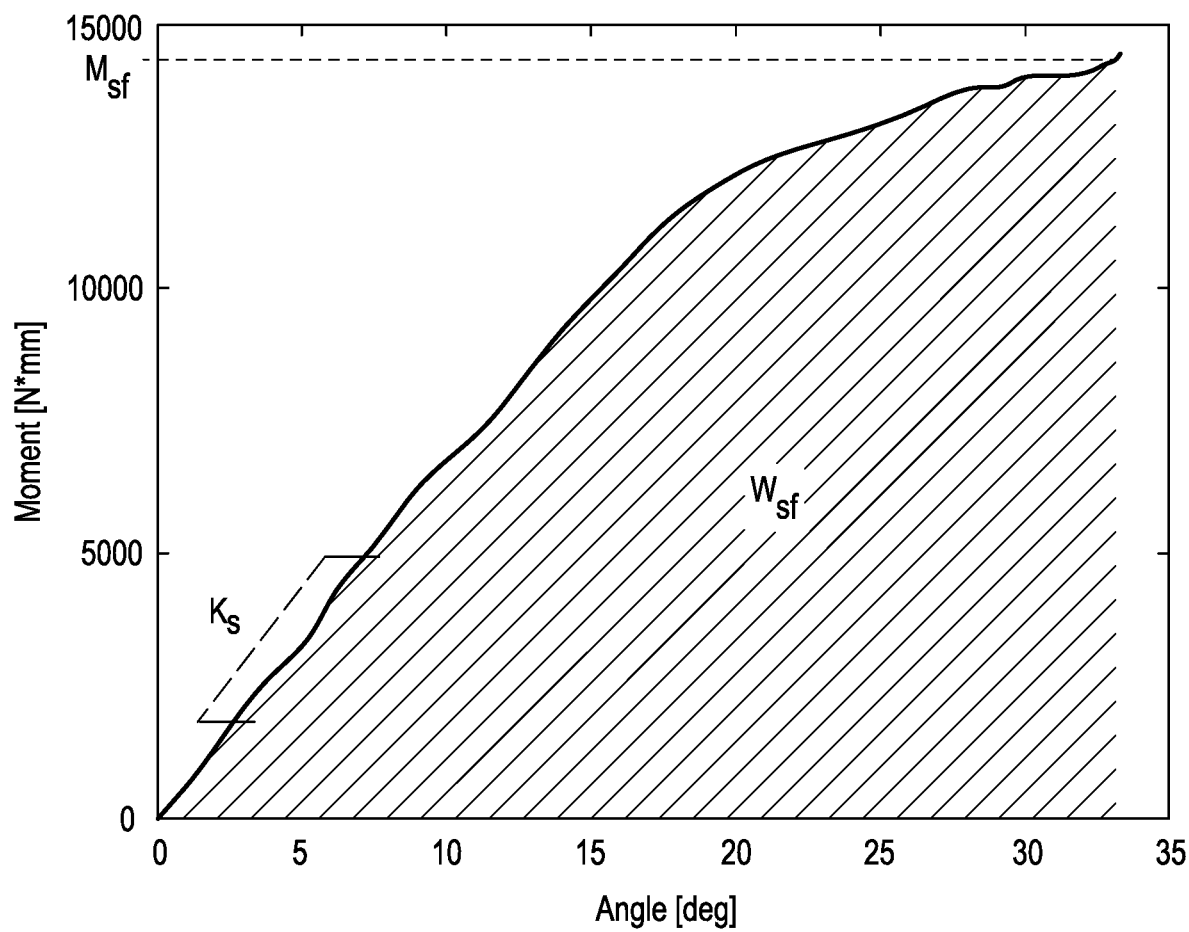
FIG. 4 is a graph that illustrates the biomechanical quantities underlying the operation of the sensor system.

FIG. 4 illustrates the biomechanical quantities underlying the operation of the contact stiffness sensor system. The graph depicts a manually induced stalk lodging failure of a single plant, via plots of the applied bending moment on the Y axis versus the resulting angular rotation of the stalk on the X axis. The maximum applied bending moment, measured as Msf [N*mm], is the applied load at which stalk failure occurs. This is the peak load capacity of the stalk structure, and is a very good descriptor of stalk lodging resistance. ks [N*mm/deg] is the stalk stiffness, calculated as the linear slope describing the region of the response between 15% and 35% of Msf; crucially, ks can be determined via non-destructive testing. Wsf [N*mm] is the stalk failure work, calculated as the area under the moment vs. angle curve up to Msf. This is also a very good descriptor of stalk lodging resistance.

Figure 5:
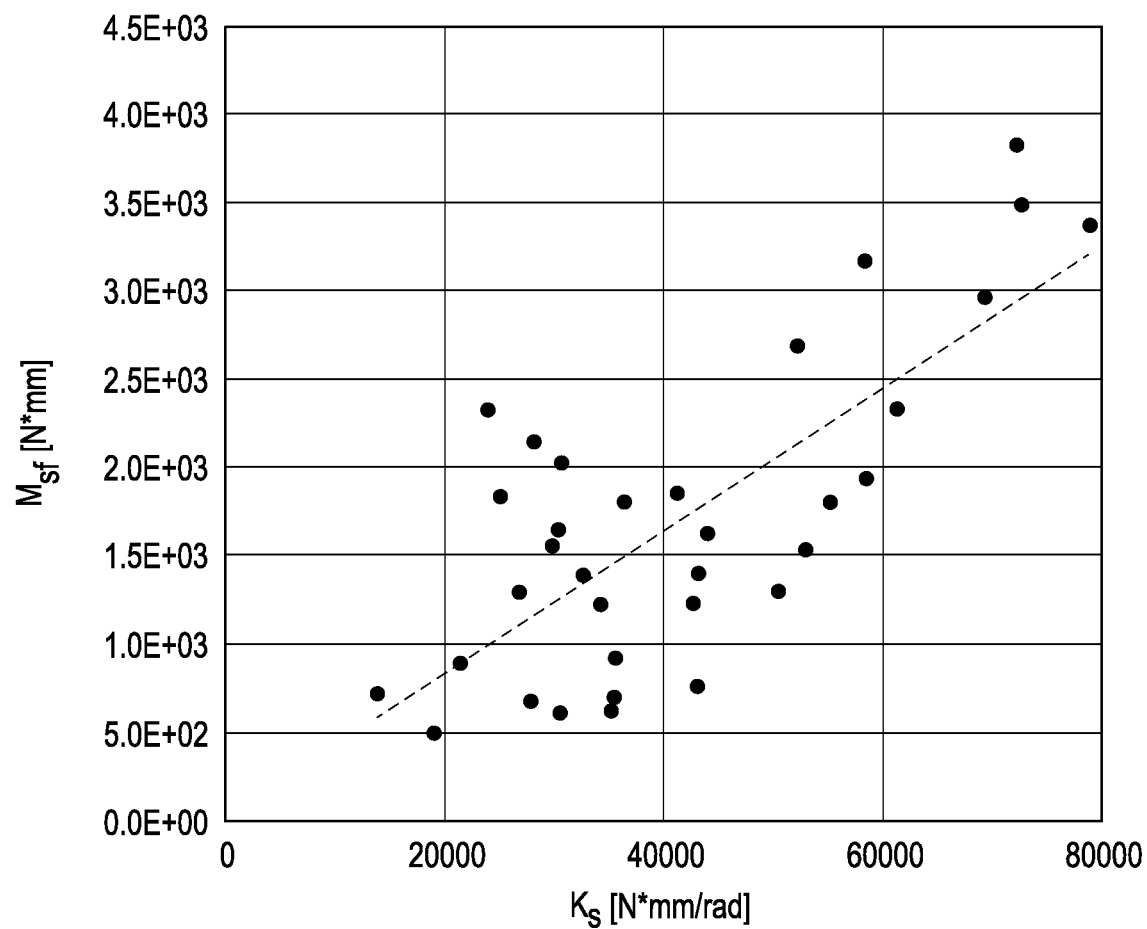
FIG. 5 is a graph that illustrates that the non-destructive measure of stalk stiffness (ks) effectively predicts stalk failure moment (Msf), a destructive measure of stalk strength that is a good descriptor of stalk lodging resistance.
Figure 6:
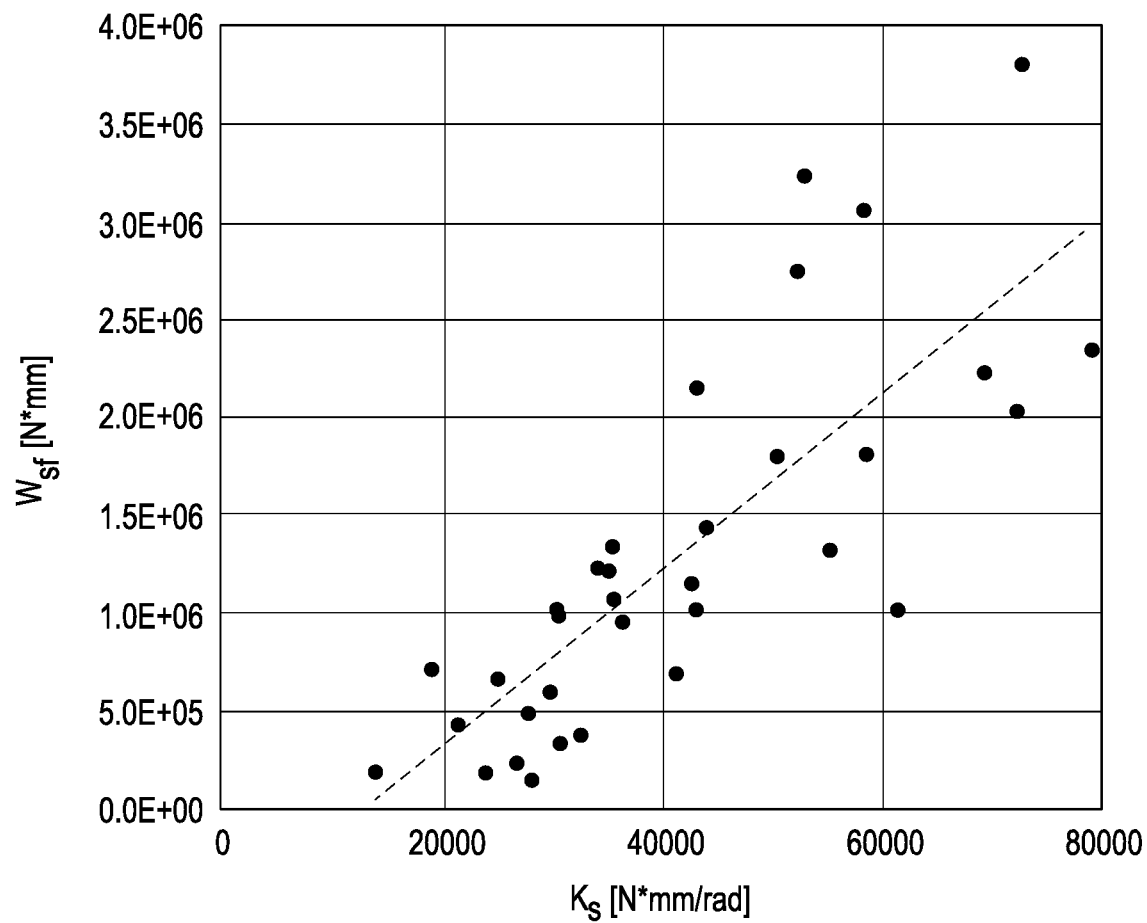
FIG. 6 is a graph that illustrates that the non-destructive measure of stalk stiffness (ks) effectively predicts stalk failure work (Wsf), a destructive measure of stalk strength that is a good descriptor of stalk lodging resistance.

FIGS. 5 and 6 illustrate that the non-destructive measure of stalk stiffness (ks) effectively predicts destructive measures of stalk strength that are very good descriptors of stalk lodging resistance. FIG. 5 illustrates that stalk stiffness ks effectively predicts stalk failure moment Msf. FIG. 6 illustrates that stalk stiffness ks effectively predicts stalk failure work Wsf. These results indicate that a plant stalk assay may be conducted without the need to reach the point of breakage, thereby enabling a non-destructive assay that provides an accurate assessment of stalk lodging resistance via a measure of stalk stiffness. By utilizing the variable rate tensioner, the contact elements (3) can be adjusted to a point where they provide an accurate measure of the stalk stiffness, and from that an indication of the point of stalk failure, without causing an actual stalk failure of the plant. The variable rate tensioner may also be adjusted to account for variable rates of travel of the agricultural vehicle, stalk differences as a result of plant variety differences, stalk differences as a result of different field or management zone locations, and/or stalk differences as a result of different agronomic practices (e.g. changes to plant population density).

Figure 7:
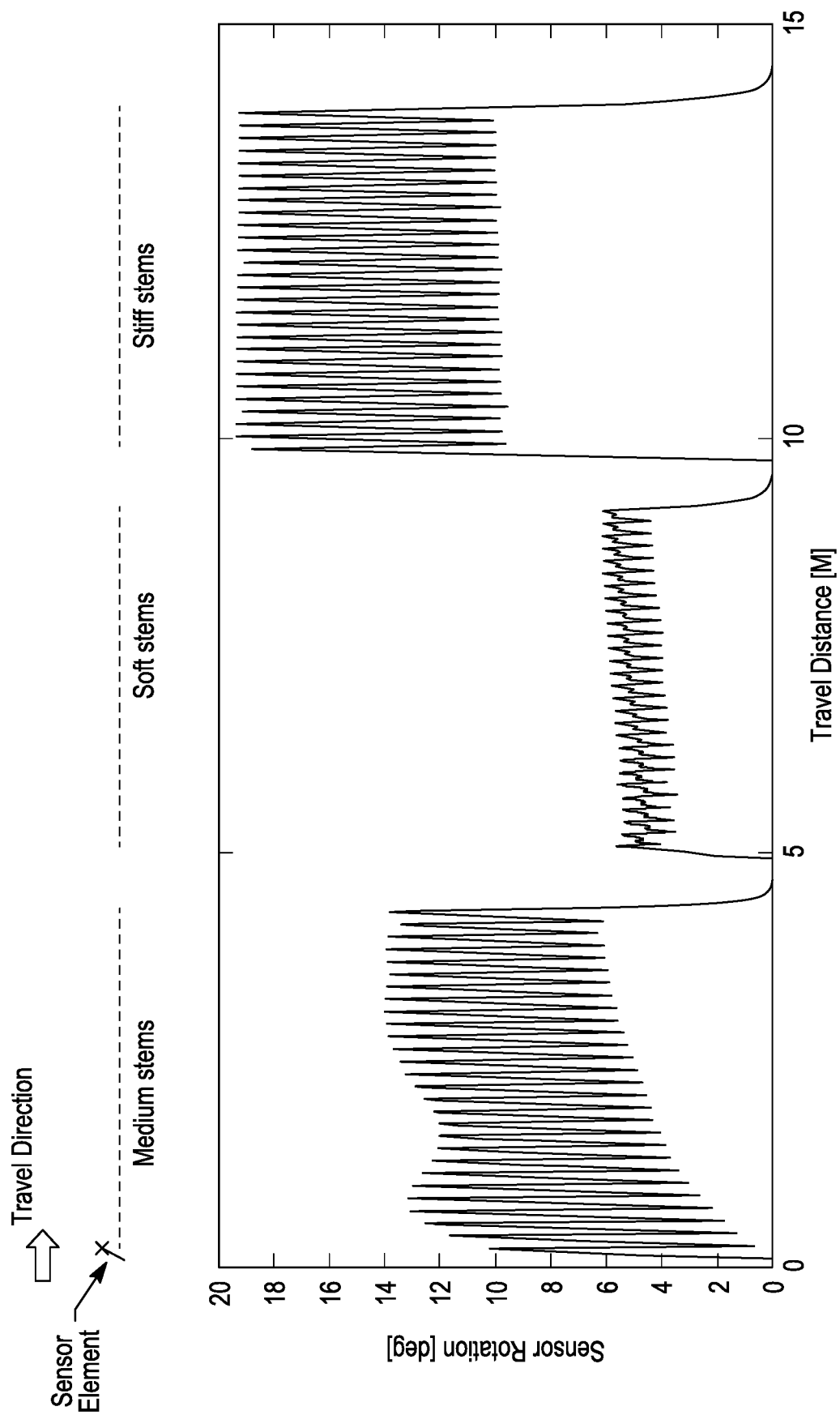
FIG. 7 is a graph that illustrates the physical simulation of a single contact sensor element with a constant spring tension traversing multiple rows with plants of different stalk stiffness, and that the different plant varieties are clearly differentiated by the sensor.

FIG. 7 illustrates the physical simulation of a contact element (3) with a constant spring tension traversing (in this case, at V=10 mph) multiple rows with plants of different stalk stiffness, as determined from in-field bio-mechanical measurements of late season maize. The sensor simulation represents the stalk stiffness configuration, rather than root anchorage configuration. The three varieties are clearly differentiated by the single sensor. Note that the encoder does not return to neutral position, due to the relatively high speed through the field, the setting for the spring constant, and the length of the contact element. The sensor rotation, measured by the rotational encoder, is used to determine the stalk stiffness via the equations described herein.

Figure 8:
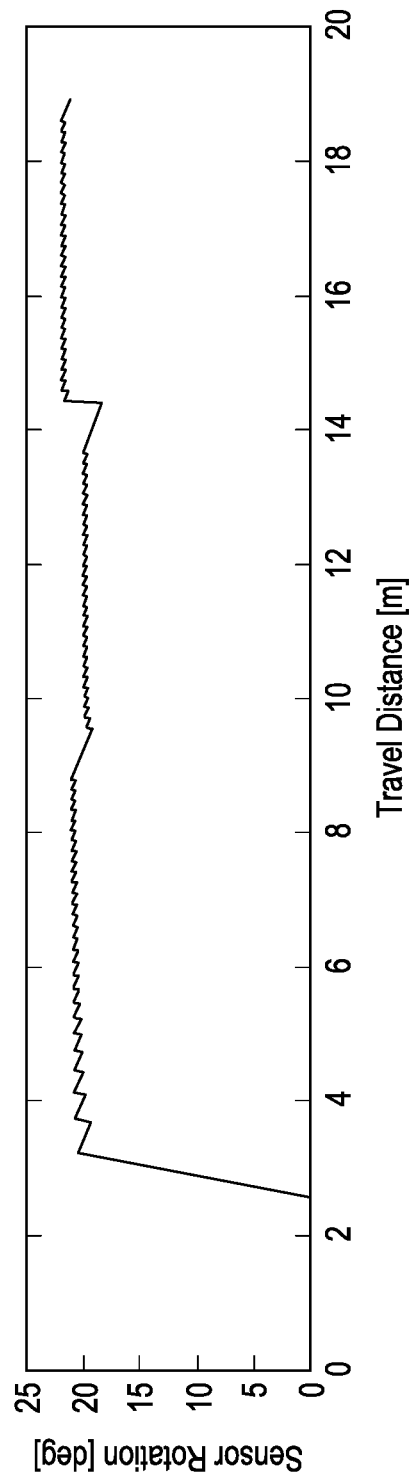
FIG. 8 is a graph that illustrates the importance of a variable rate tensioner to adjust the spring stiffness on the contact element to a level appropriate for the specific in-field conditions or management zone, and shows that when the tension is too soft and the system is 'under-stiff', the system is unable to differentiate the stiffness of the three different varieties of plants.
Figure 9:
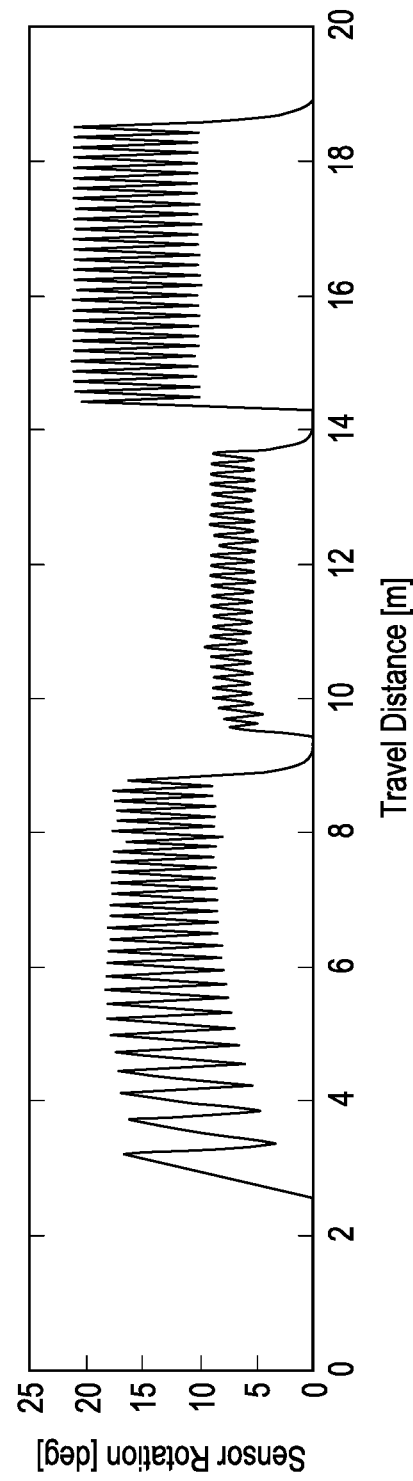
FIG. 9 is a graph that illustrates the importance of a variable rate tensioner to adjust the spring stiffness on the contact element to a level appropriate for the specific in-field conditions or management zone, and shows that a sensor with an appropriately valued spring constant effectively differentiates between diverse values of stalk stiffness.
Figure 10:
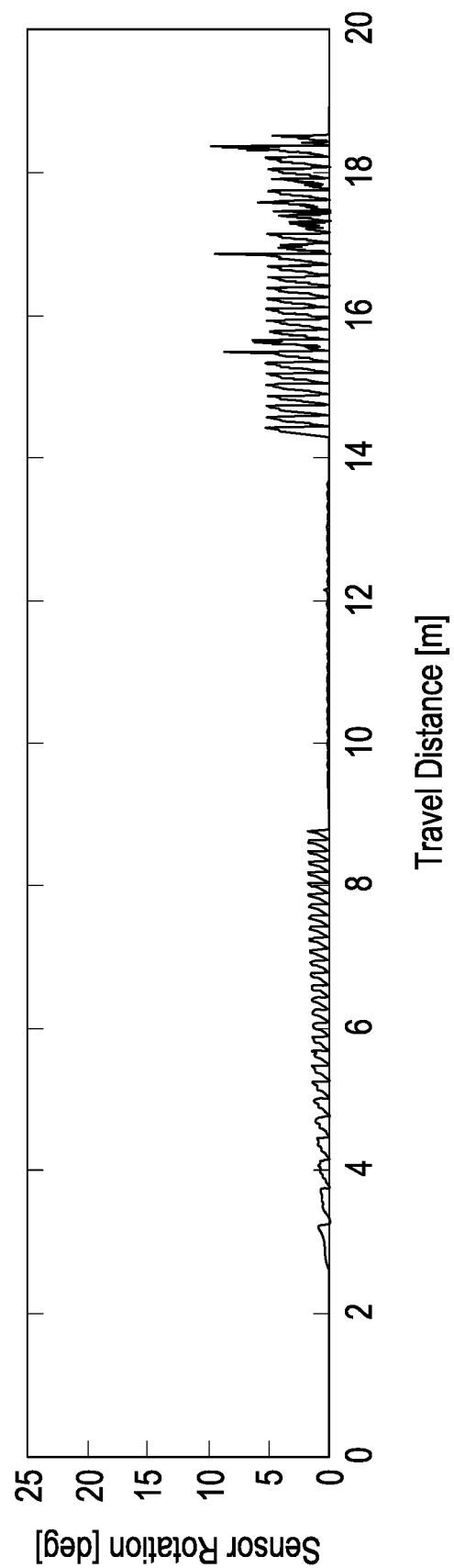
FIG. 10 is a graph that illustrates the importance of a variable rate tensioner to adjust the spring stiffness on the contact element to a level appropriate for the specific in-field conditions or management zone, and shows that when the tension is too stiff, the system is unable to detect the stiffness of two of the varieties of plants, as their stiffness values are below the lower detection limit of the over-stiff system's configuration.

FIGS. 8, 9 and 10 illustrate the importance of the variable rate tensioner to adjust the spring stiffness on the contact element to a level appropriate for the specific in-field conditions or management zone. In each of these three figures, the graph illustrates the physical simulation of constant spring sensor traversing (in this case, at V=5 mph) multiple rows with plants of different stalk stiffness, running in stalk mode. In FIG. 8, the tension is too soft to generate an effective spring constant, and so the contact element (3) is not stiff enough to meaningfully displace the plants and thus lacks the ability to detect stalk stiffness due to 'spring-dominated' displacement and insufficient recovery time. FIG. 9 illustrates that a sensor with an appropriately valued effective spring constant differentiates between diverse values of stalk stiffness, with sufficient recovery speed to discriminate between individual plants, and the stalk stiffness differences between the three groups of plants tested are clearly visible. FIG. 10 illustrates that a sensor with too stiff of an effective spring constant showed good recovery time, but resulted in 'plant-dominated' displacement conditions because the plants were too compliant with respect to the spring to induce any rotation of the very stiff sensor element, and thus the system was unable to detect the stiffness of these plants, as they were below the detection limit of the system's configuration.

Figure 11:
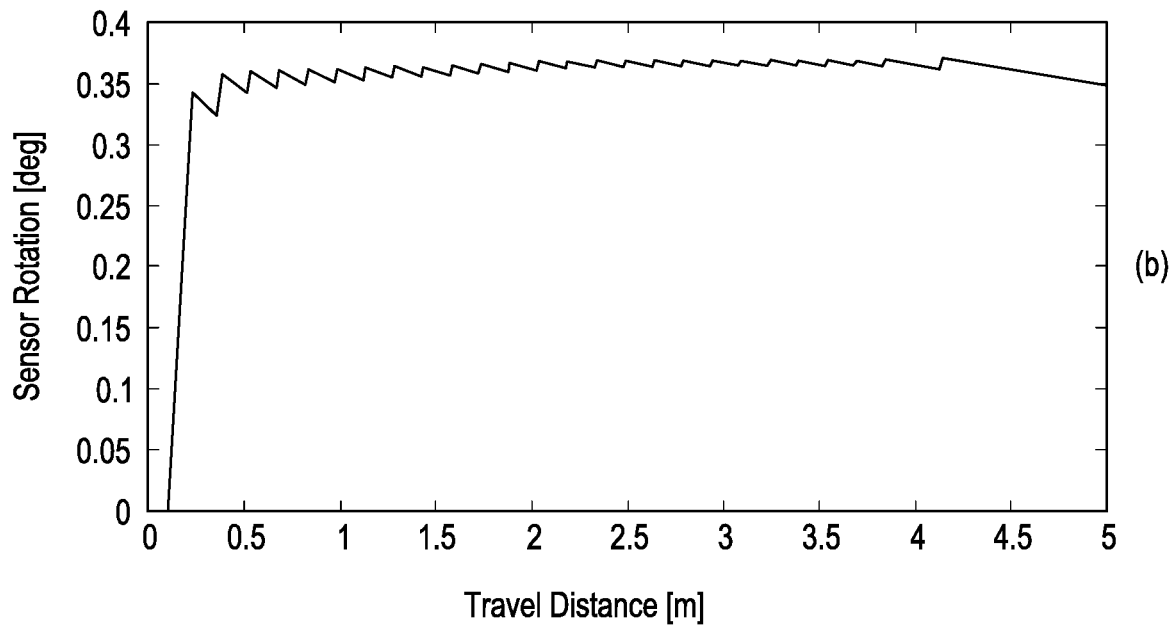
FIG. 11 is a graph that illustrates the effectiveness of the dynamically controlled variable rate tensioner, and shows that when the tension is too soft, the system does not effectively measure the individual plant stems.
Figure 12:
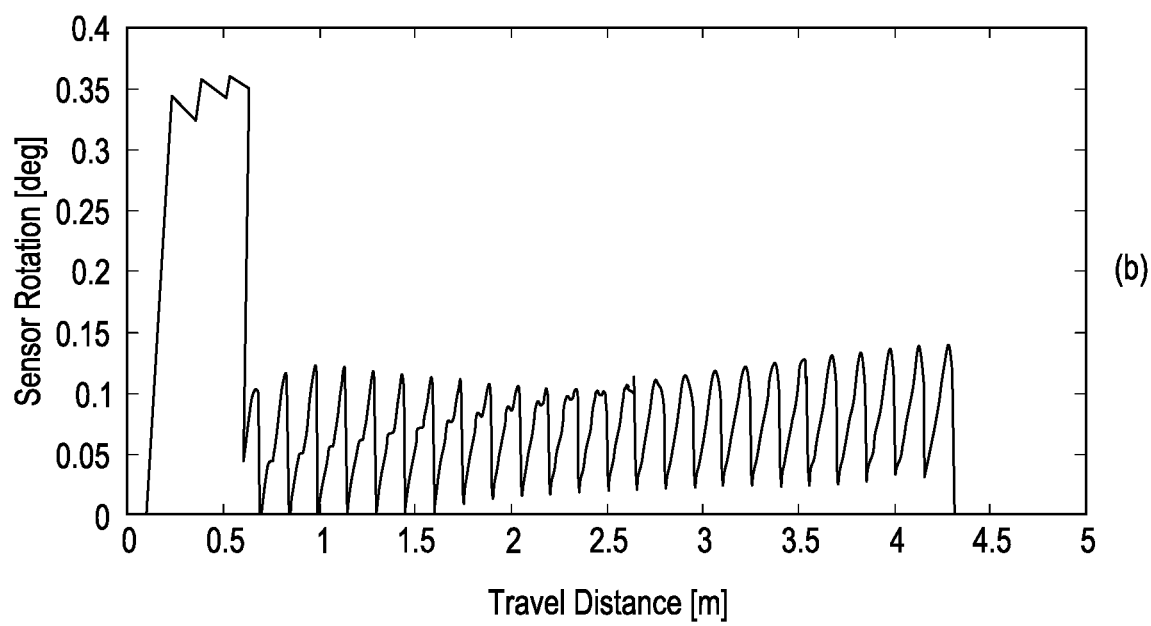
FIG. 12 is a graph that illustrates the effectiveness of the dynamically controlled variable rate tensioner, and shows the results of an on-the-go change to the spring tension at the point where the sensor rotation drops from 0.35 to 0.05, which is the point at which excessive rotation will trigger the automatically controlled system to adjust the sensor spring constant in order to improve detection.

FIGS. 11 and 12 illustrate the functionality of a dynamically controlled variable rate tensioner. FIG. 11 illustrates results from a sensor with a spring that is too soft to effectively measure the individual plant stems (similar to FIG. 8). FIG. 12 illustrates the results of an on-the-go change to the spring tension, after about 0.5 meters of travel distance, based on sensor measurements of excessive measured rotation triggered by a dynamic change to the spring constant. In some embodiments, the control of the variable rate tensioner may be remotely and dynamically adjusted, automatically or by a remote operator, to a value that improves the measurement effectiveness of the sensor system.

Additional sensor components, such as laser distance measurement devices, can be added to further enrich measured data. In addition to determining stalk stiffness, the device can also be configured to determine the anchorage stiffness as an indicator of the root lodging resistance of the plant. This is referred to as root mode (as versus stalk mode). Additional sensor inputs, such as measures of soil mechanical resistance can be utilized to enrich anchorage stiffness measurements.

Dynamics and Kinematics of Sensor Functionality

Functionality of the sensor system is described for a single contact element as follows. The variable rate tensioner is set to provide a starting spring constant such that when the contact element engages the stalk it rotates about its shaft, which includes the rotational encoder, while the stalk deflects at its base. Immediately before the contact is initiated, the contact element is at resting angle $\alpha$. The rotational spring is unloaded, so the rotational encoder is at zero position ($\theta=0$).

After contact is initiated, angular rotation of the contact element and deflection of the stalk continue to increase. Eventually, the contact element slips off from the stalk, evident in the measurement signal from the encoder as a sharp decrease in $\theta$. The maximum value of $\theta$, $\theta$ max, is recorded and its product with the rotational stiffness of the spring (krot) gives the maximum applied bending moment Mmax. The force measured by the rotational encoder is $(k_{rot} \cdot \theta_{max})/L_{fin}$ at the maximum contact angle, and the plant stalk (or stem) is deflected from its original position due to applied force. In stalk mode, it is assumed that the strength of the soil and height of the contact sensor are such that the base of the plant is fixed, and all stalk displacement is due to flexure of the stalk.

When the system is running in roots mood, $\theta$ max, dh, and several system parameters are used to determine the angle of stalk base rotation $\phi$ caused by Mmax. The ratio of M max and $\phi$ is the anchorage stiffness of the plant, which quantifies the flexibility of its anchorage system from the soil and near-surface root volume. In this case, hydration of the surrounding soil to sufficient moisture may be necessary to improve measurement resolution. Stalk mode functionality is similar, with the exception of differences in analytical data reduction. Additionally, stalk measurements should ideally be taken when the soil is at low moisture conditions and thus at maximum strength and stiffness, in order to avoid confounding the stalk deflection measurements with deformation of the anchorage system.

Figure 16:
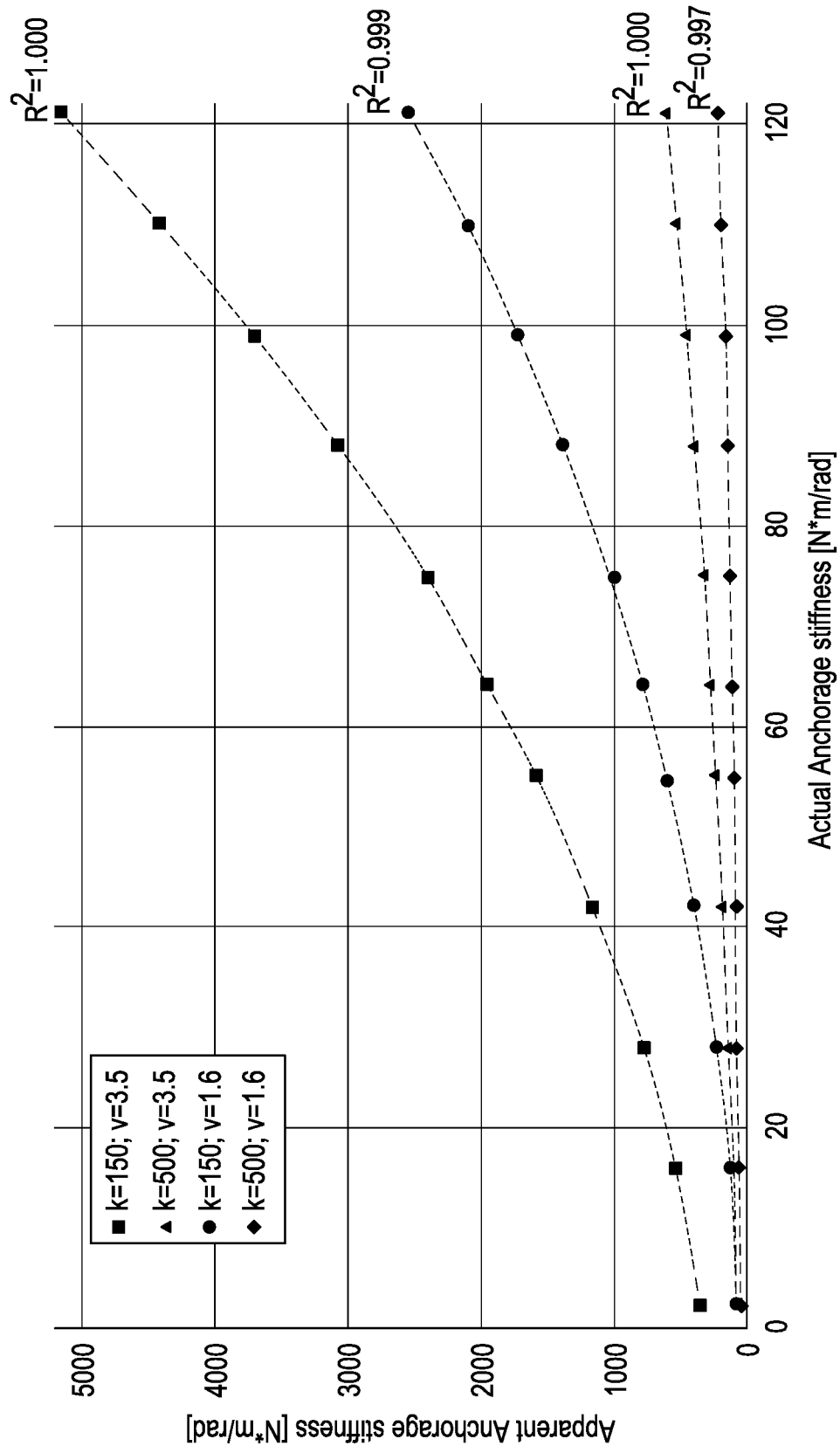
FIG. 16 is a graph that shows that apparent measured anchorage stiffness from a single sensor element versus the actual anchorage stiffness, and that there are strong relationships between the apparent measured stiffness values and the actual stiffness values, demonstrating that a model can reliably compensate for dynamic effects.

Additional system components are used to verify, refine and enrich collected data. Accelerometers verify a proper contact pattern between stalk and contact element, as well as providing the means to interpret impact and dynamic loading effects if present. On this point, the system is designed with resonant frequencies well outside the fundamental natural frequency of the plants (~1 Hz), and also includes component dampers to minimize dynamic oscillation. However, impact effects are present due to the travel speed of the field vehicle, and in embodiments of this invention, vehicle travel speed is accounted for, such as by application of a data reduction simulation model as illustrated in FIG. 16. Measurement of vehicle speed in conjunction with tracking of the spring rate applied by the adaptive tensioner allows for compensation correction for variable loading rates and impact dynamics, which may alter the measured stiffness values in both root and stalk modes, respectively.

Figure 13:
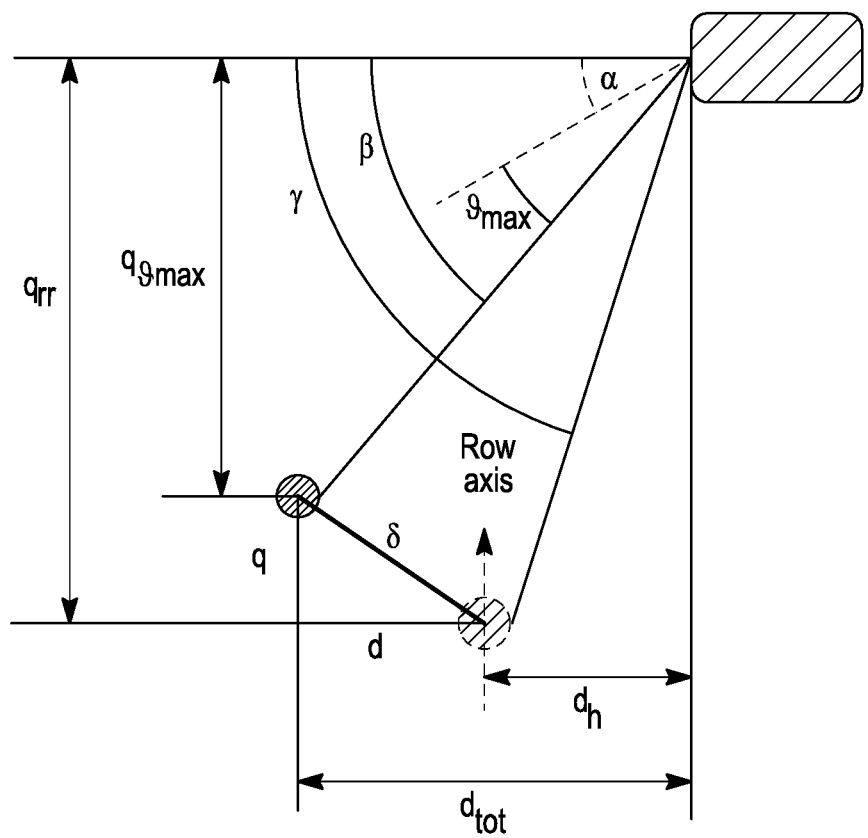
FIG. 13 illustrates various kinematic quantities associated with system functionality in a top plane view. Distances (qrr) and (qθ max) are distances [cm] associated with the various angular quantities ($\alpha$, $\beta$, $\gamma$, $\theta$ max) and the horizontal distance (dh).

FIG. 13 illustrates various kinematic quantities associated with system functionality in a top plane view. Distances $q_{rr}$ and $q\theta$ max are distances [cm] associated with the various angular quantities ($\alpha$, $\beta$, $\gamma$, $\theta$ max) and the horizontal distance dh, which is measured from the variable quantity of contact element lengths, a laser distance system, or some other means.

Figure 14:
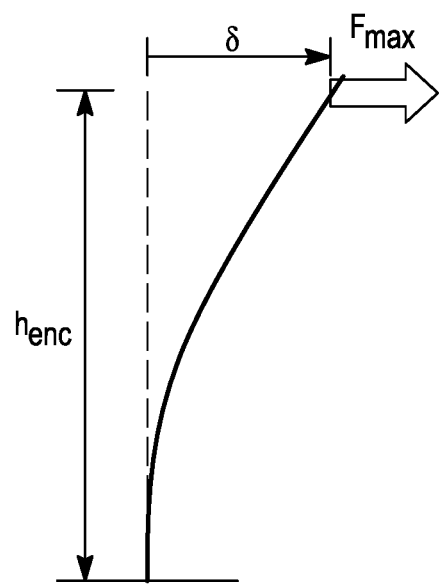
FIG. 14 illustrates the angles of flex, and formula for the device used in stalk mode to relate system parameters and values for stalk stiffness.

Formulas for the device used in stalk mode to relate system parameters and measured values to plant stalk stiffness are provided in FIG. 14 and below. With reference to FIG. 14, the contact element may be set to contact the stalk at a position informative for stalk weakness or fungal disease. This may be just below the first internode, or at a point on the second or third internodes.

The formula for the device, when used in stalk mode to relate system parameters and values for stalk stiffness, is:

$$k_s = F_{max}/\delta$$

The formulas for calculating applied loads are:

$$M_{max} = k_{rot} \cdot \theta_{max}$$

$$F_{max} = M_{max}/L_{fin}$$

$$M_{app} = F_{max} \cdot h_{enc}$$

The formulas for calculating plant deflection $\delta$ are:

$$d = d_{tot} - d_h = L_{fin}(\cos \beta - \cos \gamma)$$

$$q = q_{rr} - q_{\theta\ max} = L_{fin}(\sin \gamma - \sin \beta)$$

$$\delta = \sqrt{q^2 + d^2} = L_{fin} \cdot [2 - 2\cos(\beta - \gamma)]$$

The formula for calculating stem stiffness (ks) via system parameters and measured quantities is:

$$k_s = \frac{F_{max}}{\delta} = \frac{\left(\dfrac{k_{rot} \cdot \theta_{max}}{L_{fin}}\right)}{L_{fin} \cdot [2 - 2\cos(\beta - \gamma)]}$$

Figure 15:
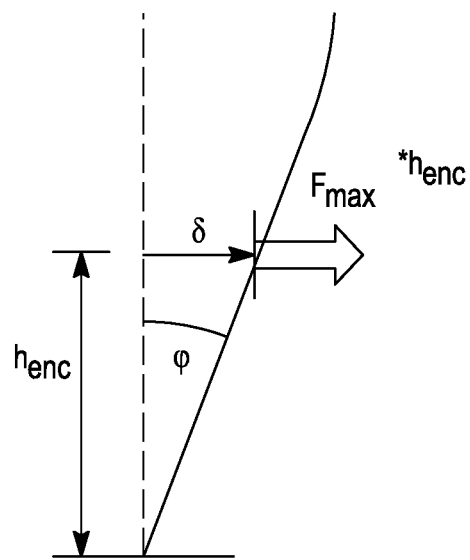
FIG. 15 illustrates the angle of flex, and formula for the device used in root mode to relate system parameters with values for root anchorage stiffness.

Formulas for the device used in root mode, to relate system parameters and measured values to plant anchorage stiffness, are presented in FIG. 15 and below. With reference to FIG. 15, when operating in root mode it is advantageous for the contact element to contact the stalk at a lower point towards the base of the plant in order to avoid confounding measurements of rotation in the anchorage system with deflections of the stalk.

Calculating applied loads and calculating plant deflection ($\delta$) are as described above.

The formula for the device used in root mode to relate system parameters with values for root anchorage is:

$$k_a = M_{app}/\varphi$$

The formulas for calculating anchorage stiffness (ka) via system parameters and measured quantities are:

$$k_a = \frac{M_{app}}{\phi} = \frac{h_{enc} \cdot F_{max}}{\tan^{-1}(\delta/h_{enc})} = \frac{h_{enc} \cdot \left(\dfrac{k_{rot} \cdot \theta_{max}}{L_{fin}}\right)}{\tan^{-1}\left(\dfrac{L_{fin} \cdot [2 - 2\cos(\beta - \gamma)]}{h_{enc}}\right)}$$

The description of the quantities in FIGS. 13-15 are as follows:

$\alpha$ = encoder resting angle [rad] (system parameter).

krot=rotational stiffness [N*m/rad] of embedded (mechanical, hydraulic, pneumatic, electromagnetic) variable rate tensioner (system parameter).

Lfin=length [cm] of contact element (system parameter).

V0=average speed [m/s] of vehicle (measurement).

θ max=actual maximum measured angle [rad] (measurement).

γ=theoretical maximum total angle [rad] (calculated).

dh=horizontal distance [cm] from encoder to plant row (measurement).

dtot=horizontal distance [cm] from encoder to deflected plant (calculated).

qrr=transverse distance [cm] from encoder to initial location of plant (calculated).

qθ max=transverse distance [cm] from encoder to deflected plant (calculated).

δ=deflection [cm] of plant; necessary for stiffness calculation (calculated).

henc=height [cm] of encoder (system parameter).

M max=applied bending moment [N*m] from contact element contacting stalk (calculated).

F max=applied force [N] associated with Mmax (calculated).

φ=angle [rad] of plant stem deflection (calculated).

ks=stalk stiffness [N/m] (calculated).

ka=anchorage stiffness [N*m/rad] (calculated).

FIG. 16 shows a plot of apparent measured anchorage stiffness from a single sensor element, calculated via the equation for anchorage stiffness (ka) using system parameters and measured values, versus the actual anchorage stiffness input to the simulation model. Depending on the vehicle travel speed and spring rate, there can be significant dynamic effects that increase the apparent measured stiffness with respect to the actual stiffness. A simulation model, such as the one used to produce the results in FIG. 16, that incorporates the vehicle travel speed and spring rate as parameters can be used to resolve the actual stiffness from the apparent measured value. In all cases (i.e. for all values of vehicle travel and spring rate), there are strong relationships between the apparent measured stiffness values and the actual stiffness values, demonstrating the validity of the simulation model as a data reduction tool. The plot shows that the sensor system effectively differentiates between plants with different anchorage stiffness values regardless of the operating parameters (spring rate and vehicle travel speed), and that knowledge of these operating parameters allows the apparent stiffness to be reduced to the actual stiffness via the simulation model. Also, it shows that some combinations of travel speed and spring rate reduce the difference between apparent measured and actual stiffness (i.e. higher spring constant and lower velocity), indicating that in addition to improving detection range of the sensor system, a dynamically controlled variable rate tensioner is also a means by which to improve system accuracy for cases where a simulation model or its output are not used in the data reduction/analysis process.

Figure 17:
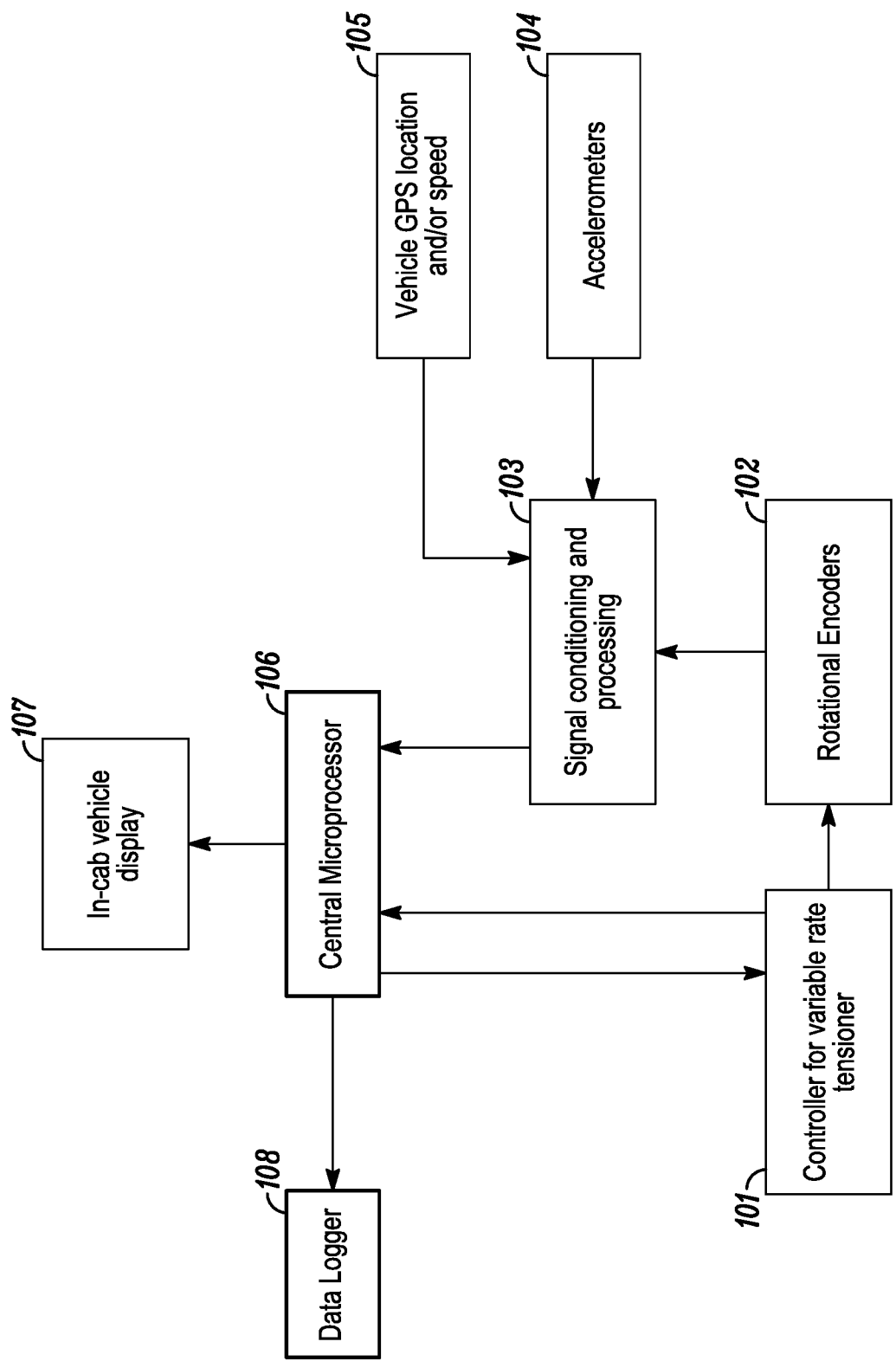
FIG. 17 describes a process flow chart for the contact sensor system operating in 'stalk mode'.

FIG. 17 describes a process flow chart for the contact sensor system operating in 'stalk mode'. The controller for the variable rate tensioner (101), the rotational encoder (102), the accelerometer (104), and the vehicle GPS location and/or speed (105) are all fed to the central microprocessor (106), either directly or indirectly through a signal conditioning and processing unit (103). The output may be presented to a vehicle display (107) and is logged via a data logger (108).

Figure 18:
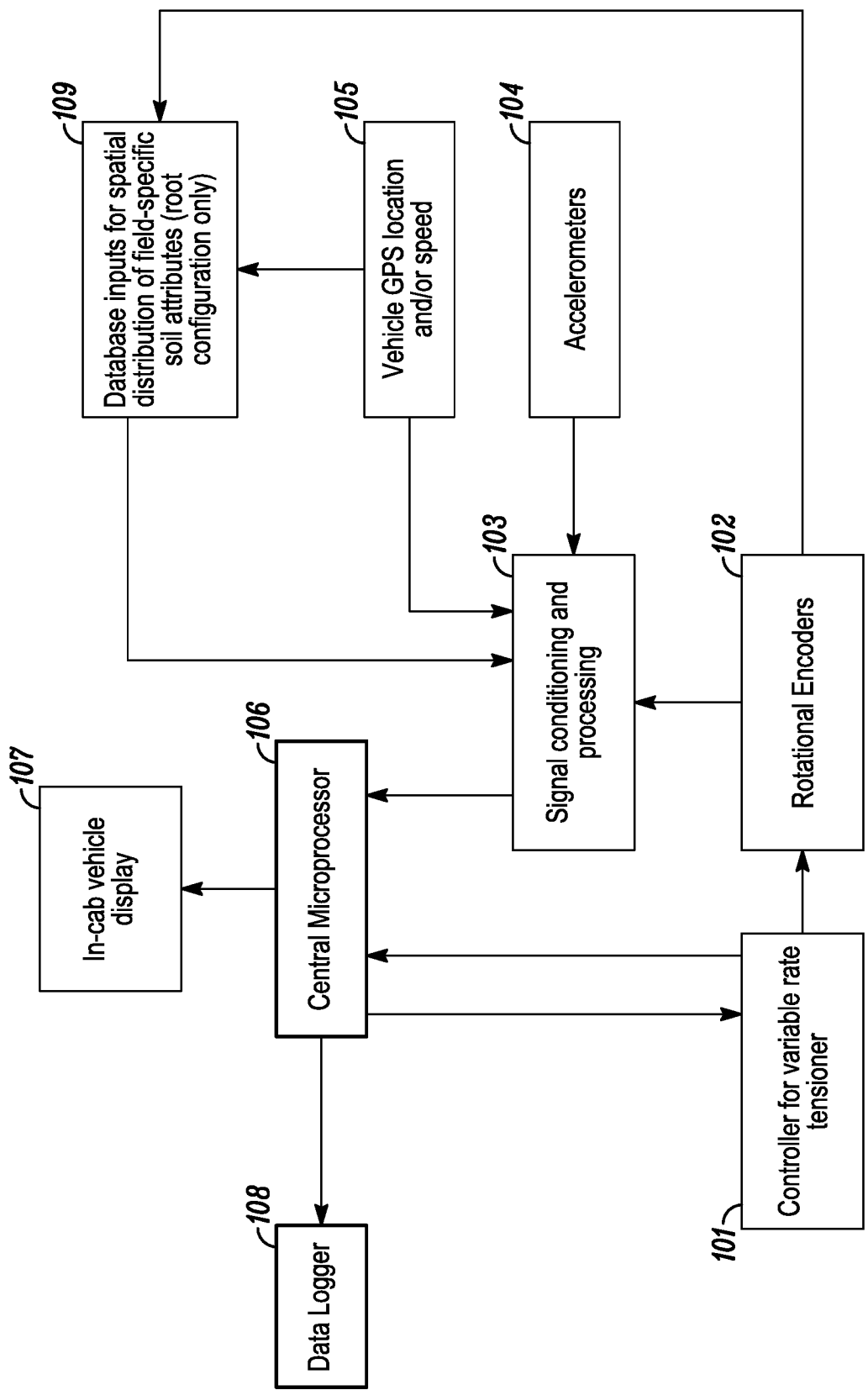
FIG. 18 describes a process flow chart for the contact sensor system operating in 'root mode'.

FIG. 18 describes a process flow chart for the contact sensor system operating in 'root mode'. Elements are the same as described in FIG. 19, with the addition of database inputs for spatial distribution of field-specific soil attributes (109), such as soil mechanical resistance or other quantities derived therefrom.

Stalk and Root Pathology Considerations

As noted above, stalks that are infected with a fungal disease may be more susceptible to stalk lodging due to weakening in the stalk that may be caused by the fungal pathogens. Fungal pathogens that may contribute to stalk lodging include, but are not limited to, Anthracnose stalk rot (*Colletotrichum graminicola*), *Fusarium* stalk rot, Gibberella stalk rot, Charcoal rot (*Macrophomina phaseolina*) and *Diplodia* stalk rot. Bacterial disease may also result in stalk weakening, such as *Erwinia chrysanthemi* pv. *Zeae* as one example. Burrowing into the stalk by insects, such as the common stalk borer, European corn borer, corn earworm, hop vine borer, fall armyworm, southwestern corn borers and/or lesser cornstalk borer, also weakens the stalk and can serve as a site of fungal and/or bacterial infection.

Accordingly, the assay device may be used to assess stalks for damage from pathogens, whether such pathogens are due to fungal infection, bacterial infection and/or insect damage.

One specific use of the stalk sensor is to assess corn borer damage in a research field. A research field may comprise a defined area of plants intentionally infected (inoculated) with corn borers, typically at the second stalk node above the brace roots. Since the location of infection is known, this can be used to set the height of the stalk assay device so that the contact elements span the area of the stalk where the inoculation occurred. The use of the contact elements in combination with electrical conductivity measurements, or measurements from one or more of the other devices mentioned above, can be used to further estimate the extent of the stalk damage in such a test field. At least two contact elements can be positioned on either side of the inoculation location, and a reduced electrical conductivity measurement may be indicative of stalk damage. Further, different internodes can be examined to identify the location of stalk damage and/or disease, even in cases where the location of the infection is not known ahead of time. The speed of measurement of the stalk assay device described herein can be a significant advantage over slower and/or more destructive devices. The nondestructive sensor functionality also allows for repeated measurement to evaluate the progression of stalk disease and/or damage during the crop season.

Similarly, root zones that have been compromised by corn root worm feeding may be more susceptible to root lodging due to reduction of the effective root zone size, as well as reduction of key root structural mass. Prevalent varieties of rootworm include Western Corn Rootworm (*Diabrotica virgifera*), Northern Corn Rootworm (*Diabrotica barberi*), Southern Corn Rootworm (*Diabrotica undecimpunctata howardi*), and Mexican Corn Rootworm (*Diabrotica virgifera zeae*). The assay device may be used to assess plants to detect damage to root zones and increased root lodging susceptibility from rootworm feeding.

Further Embodiments

The assay device of the present invention may also be used in conjunction with other devices that together will give an in-depth analysis of the stalk morphology. Technologies that can be combined with the present assay device include non-destructive and/or non-invasive techniques such as using an in-field CT scanner, a terahertz imaging system, sonar, thermal acoustic imaging, magnetic resonance imaging, ultrasound imaging, functional magnetic resonance imaging (FMRI), infrared imaging x-ray imaging, laser pulses, visible light imaging and ground penetrating radar. The imaging technology could be optimized to highlight the different times of reflectance as electromagnetic waves propagate through the rind and pith of the stalk, which would help to quantify degrees of stalk rot, insect tunneling and fungal infection.

In addition, a moisture probe can be combined with the present device to measure available soil moisture, since moisture can have a significant effect on plant health, as well as influencing anchorage stiffness through altering soil strength. Electrical conductivity can be used to measure differences in electrical current between one or more sets of the sensor contact elements, with an infected or structurally damaged stalk less able to effectively conduct electricity. Since resistance is proportional to the distance between the electrodes, such electrodes can be positioned at the ends of the contact elements and used to calculate electrical conductivity through a portion of the plant stalk. Pathogenic infection between the two points of contact (the contact elements) may be indicative of unhealthy plant tissue.

The stalk stiffness sensor described herein may also be coupled with data from drone imaging or other in-row imaging devices to further refine the measurement data, particularly for plant and ear height sensing, which data can also be informative for root and stalk lodging susceptibility.

What is claimed is:

1. A sensor system for detecting properties of a plant in a field, said sensor system comprising:
   a plurality of contact elements, at least some of which contact the plant,
   a sensor operably connected to each contact element, whereby the sensor measures the mechanical force resulting from the mechanical interaction between the contact element and the plant, and
   a tensioner operably connected to each contact element, wherein each tensioner may be remotely adjusted, and wherein each tensioner provides mechanical resistance to the motion of the contact element.

2. The sensor system of claim 1, wherein the sensor is a rotational sensor that measures the angular rotation of the contact element as it contacts the plant.

3. The sensor system of claim 1, wherein each tensioner may be remotely adjusted to the same tension based upon the force recorded by at least one contact element.

4. The sensor system of claim 1, wherein the remote adjustment occurs automatically.

5. The sensor system of claim 4, wherein the automatic adjustment is based on sensor feedback.

6. The sensor system of claim 5, wherein the sensor feedback is adjusted to reduce the force caused by vehicle movement in the direction of travel.

7. The sensor system of claim 1, wherein the rotational sensor comprises a rotational encoder.

8. The sensor system of claim 1, wherein the rotational sensor comprises a load cell.

9. The sensor system of claim 1, wherein the plant property detected is stalk stiffness.

10. The sensor system of claim 1, wherein the sensor system is attached to a farm vehicle.

11. The sensor system of claim 1, wherein the plurality of contact elements are connected to a frame, and the angle of each contact element with respect to the frame may be remotely adjusted.

12. The sensor system of claim 1, wherein there are at least two contact elements on each side of the sensor system so that properties of two rows of crops can be detected at the same time.

13. The sensor system of claim 1, wherein each contact element further comprises an accelerometer.

14. The sensor system of claim 1, wherein the contact element comprises a non-deformable material operably connected to an adjustable tensioner.

15. The sensor system of claim 1, wherein the contact element is deformable.

16. A method of assaying at least one property of a plant in a field using a sensor system, comprising moving the sensor system past a row of plants, said sensor system comprising contact elements, and allowing at least some contact elements on the sensor system to contact the plants in the row, detecting the force acting on the contact elements as they contact the plants and correlating the force with at least one plant property, wherein the mechanical resistance of at least one contact element on the sensor system may be remotely adjusted.

17. The method of claim 16, wherein the plant property is resistance to stalk lodging.

18. The method of claim 16, wherein the plant stalk is not damaged by the sensor system.

19. The method of claim 16, wherein the plant property is ear height.

20. The method of claim 16, wherein the sensor system is attached to a farm vehicle.

21. The method of claim 16, wherein contact elements are connected to a frame, and the angle of each contact element with respect to the frame may be remotely adjusted.

22. The method of claim 16, wherein there are at least two contact elements on each side of the sensor system.

23. A method of assaying plants inoculated with a pathogen, comprising moving a sensor system past a row of plants inoculated with a pathogen at a known location on the stalk of said plant, said sensor system comprising contact elements and allowing at least some contact elements on the sensor system to contact the plants in the row at the point of inoculation, wherein the sensor system is positioned to detect the force of the contact elements as they contact the plant and correlating the force with the level of stalk damage caused by the stalk boring insect, wherein the mechanical resistance of at least one contact element on the sensor system can be remotely adjusted.

24. The method of claim 23, wherein the plant is corn.

25. The method of claim 23, wherein the plant stalk is not damaged by the assay.

26. The method of claim 23, wherein at least one contact element is positioned to contact the stalk at the point of inoculation.

27. The method of claim 23, wherein at least two contact elements are positioned to contact the stalk, with one contact element being positioned above the point of inoculation, and one contact element being positioned below the point of inoculation.

* * * * *